United States Patent
Graimann et al.

(10) Patent No.: US 10,448,857 B2
(45) Date of Patent: Oct. 22, 2019

(54) POWERED, MULTI-FUNCTIONAL LIMB MOVEMENT AUXILIARY DEVICE, PARTICULARLY PROSTHESIS AND MOVEMENT-ASSISTING ORTHOSIS, WITH COMBINED ESTIMATION REGIMES

(71) Applicants: GEORG-AUGUST-UNIVERSITÄT GÖTTINGEN STIFTUNG ÖFFENTLICHEN RECHTS, Göttingen (DE); Ottobock SE & Co. KgaA., Duderstadt (DE)

(72) Inventors: Bernhard Graimann, Obernfeld (DE); Sebastian Amsüss, Vienna (AT); Dario Farina, Göttingen (DE)

(73) Assignees: Georg-August-Universität Göttingen Stiftung Öffentlichen Rechts, Göttingen (DE); Ottobock SE & Co. KgaA., Duderstadt (DE)

( * ) Notice: Subject to any disclaimer, the term of this patent is extended or adjusted under 35 U.S.C. 154(b) by 111 days.

(21) Appl. No.: 15/737,635

(22) PCT Filed: Jun. 3, 2016

(86) PCT No.: PCT/EP2016/062697
§ 371 (c)(1),
(2) Date: Dec. 18, 2017

(87) PCT Pub. No.: WO2016/202613
PCT Pub. Date: Dec. 22, 2016

(65) Prior Publication Data
US 2018/0168477 A1     Jun. 21, 2018

(30) Foreign Application Priority Data
Jun. 19, 2015   (EP) .................................. 15173019

(51) Int. Cl.
A61B 5/0488   (2006.01)
A61F 2/60   (2006.01)
(Continued)

(52) U.S. Cl.
CPC .......... *A61B 5/04888* (2013.01); *A61F 2/583* (2013.01); *A61F 2/72* (2013.01);
(Continued)

(58) Field of Classification Search
CPC .... A61F 2/54; A61F 2/583; A61F 2/72; A61F 2002/701; A61F 2002/704;
(Continued)

(56) References Cited

U.S. PATENT DOCUMENTS 5,905,648 A * 5/1999 Badami .................. D06F 33/02
700/55
9,174,339 B2 * 11/2015 Goldfarb ................. A61F 2/583
(Continued)

FOREIGN PATENT DOCUMENTS

EP   2417941 A1   2/2012
WO   WO-0113778 A2   3/2001
WO   WO-2012071343 A1   5/2012

OTHER PUBLICATIONS

Hahne, J. M. et al., "Linear and Nonlinear Regression Techniques for Simultaneous and Proportional Myoelectric Control", IEEE Transactions on Neural Systems and Rehabilitation Engineering, IEEE Service Center, New York, NY, US, vol. 22, No. 2, Mar. 1, 2014 (Mar. 1, 2014), pp. 269-279, XP011542176, ISSN: 1534-4320, DOI: 10.1109/TNSRE.2014.2305520 [retrieved on Mar. 5, 2014].
(Continued)

*Primary Examiner* — Thomas Sweet
*Assistant Examiner* — Christie L Bahena
(74) *Attorney, Agent, or Firm* — Harness, Dickey & Pierce, P.L.C.

(57) ABSTRACT

A method of operating a multi-functional limb movement auxiliary device comprising a plurality of actuators configured to move, upon activation, limb movement auxiliary device members in at least two independent degrees of freedom, a bio-signal sensing unit that is configured to acquire bio-signals indicative of motor activity, a control unit configured to receive and evaluate the acquired bio-signals, the method comprising steps of acquiring bio-signals from the user of the limb movement auxiliary device, applying a novelty detection method (ND) for comparing digitally converted, acquired bio-signals with calibration bio-signals, and, based on a result of the comparison, for assigning a similarity measure to the acquired, digitally converted bio-signals, applying at least one sequential estimator (SEQ-E) to the acquired, digitally converted bio-signals, if the assigned similarity measure is equal to or larger than a pre-determined threshold value, applying at least one simultaneous estimator (SIM-E) to the acquired, digitally converted bio-signals, if the assigned similarity measure is less than the pre-determined threshold value, and activating at least one actuator out of the plurality of actuators, based on a result of applying one of the estimators (SIM-E, SEQ-E) to the acquired, digitally converted bio-signals; and a multi-functional limb movement auxiliary device including a control unit configured for carrying out such method.

11 Claims, 3 Drawing Sheets

Figure 1:
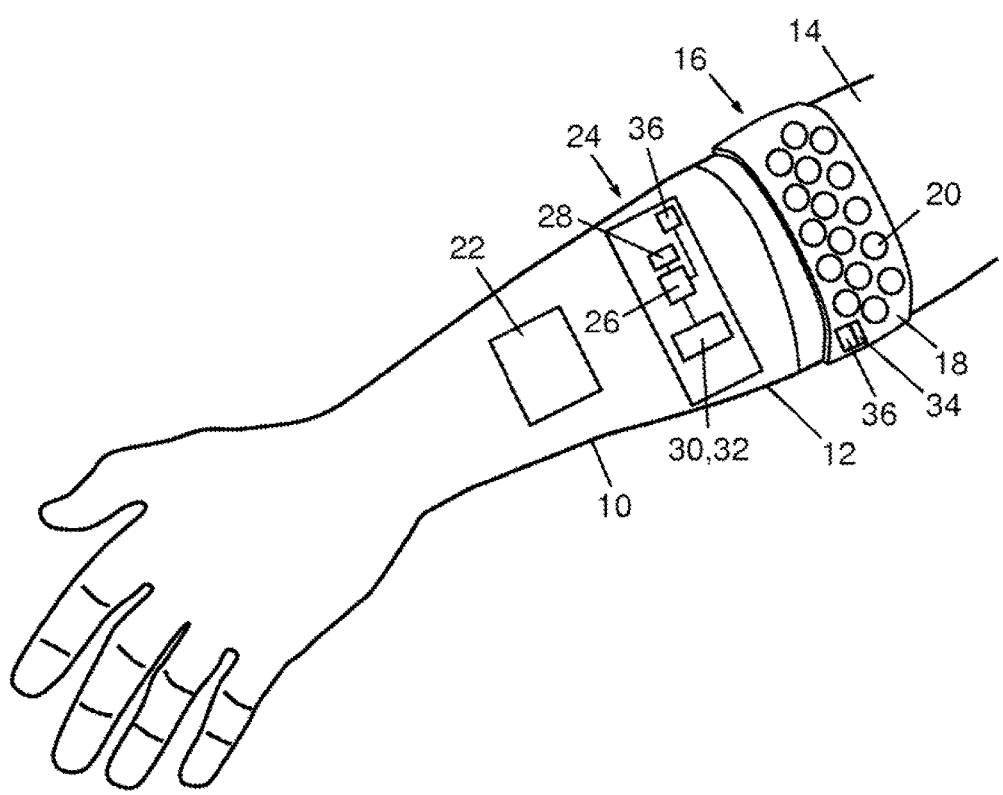

(51) Int. Cl.
    *A61F 2/58*      (2006.01)
    *A61F 2/72*      (2006.01)
    *A61F 2/54*      (2006.01)
    *A61F 2/70*      (2006.01)
    *A61F 2/76*      (2006.01)

(52) U.S. Cl.
    CPC ........... *A61F 2/54* (2013.01); *A61F 2002/701* (2013.01); *A61F 2002/704* (2013.01); *A61F 2002/7615* (2013.01); *A61F 2002/7635* (2013.01)

(58) Field of Classification Search
    CPC ..... A61F 2002/7615; A61F 2002/7635; A61B 5/04888
    See application file for complete search history.

(56) References Cited

U.S. PATENT DOCUMENTS

2014/0128992 A1    5/2014  Engeberg
2015/0156578 A1*  6/2015  Alexandridis ......... H04R 3/005
                                                    381/92

OTHER PUBLICATIONS

Fukunaga, K.: Introduction to Statistical Pattern Recognition, Second Edition, San Diego, CA, USA: Academic Press, 1990.

Markou, M. et al., "Novelty detection: a review—part 1: statistical approaches," Signal Processing, vol. 83, No. 12, pp. 2481-2497, Dec. 2003.

Schölkopf, B. et al., "Support Vector Method for Novelty Detection," NIPS, vol. 12, pp. 582-588 (1999).

Bodesheim, P. et al., "Kernel Null Space Methods for Novelty Detection", 2013 IEEE Conference on Computer Vision and Pattern Recognition, pp. 3374-3381, Jun. 2013.

Amsuess, S. et al., "A Multi-Class Proportional Myocontrol Algorithm for Upper Limb Prosthesis Control: Validation in Real-Life Scenarios on Amputees", submitted to and accepted as Early Access Paper by IEEE Transactions on Neural Systems and Rehabilitation Engineering (2014), pp. 1-10.

* cited by examiner

POWERED, MULTI-FUNCTIONAL LIMB MOVEMENT AUXILIARY DEVICE, PARTICULARLY PROSTHESIS AND MOVEMENT-ASSISTING ORTHOSIS, WITH COMBINED ESTIMATION REGIMES

This application is a National Stage of International Application No. PCT/EP2016/062697, filed on Jun. 3, 2016, and published in English as WO2016/202613 A1 on Dec. 22, 2016. This application claims priority to European Patent Application No. 15173019.9, filed on Jun. 19, 2015. The entire disclosures of the above applications are incorporated herein by reference.

The work leading to this disclosure has received funding from the European Union Seventh Framework Programme (FP7/2007-2013) under grant agreement no. 251555, AMYO.

FIELD

The disclosure pertains to a multi-functional limb movement auxiliary device, in particular to a prosthesis, a movement-assisting orthosis, an exoskeletal device and a neurorehabilitation robotic device, and to a method of operating such multi-functional limb movement auxiliary device.

BACKGROUND

This section provides background information related to the present disclosure which is not necessarily prior art.

In the art of controlling powered multi-functional limb prostheses it is known to apply machine learning methods to electromyogram signals acquired from a surface of a remaining portion of a user's limb so as to derive estimates for limb movements intended by the user.

Two main control methods have evolved in this field: classification and regression. Classification methods allow articulation of many degrees of freedom (DOF). The downside of classification is that it does not allow for arbitrary combinations of simultaneous activations across multiple DOFs, which is required to enable a natural appearance of a prosthetic movement (sequential movement estimation). The natural appearance, characterized by simultaneous and proportional control, can be facilitated by employing regression methods (simultaneous movement estimation). However, a controlling capability by using regression methods has been found to be limited to a maximum of four functions, corresponding to two DOFs.

SUMMARY

This section provides a general summary of the disclosure, and is not a comprehensive disclosure of its full scope or all of its features.

It is therefore an object of the disclosure to provide a powered, multi-functional limb movement auxiliary device that is improved with regard to natural appearance of prosthetic movements for at least two degrees of freedom (DOF).

In one aspect of the present disclosure, the object is achieved by a multi-functional limb movement auxiliary device, comprising a base member, a socket member that is configured to at least partially receive a portion or a remaining portion of a limb, and a plurality of limb movement auxiliary device members. Each limb movement auxiliary device member is connected in an articulated way to at least one out of the base member or a different limb movement auxiliary device member.

The multi-functional limb movement auxiliary device further includes a plurality of actuators that are connectable to an electric power source. Each actuator is configured to move, upon activation, at least one limb movement auxiliary device member out of the plurality of limb movement auxiliary device members in an articulated way. The plurality of actuators is configured to enable articulated movements of limb movement auxiliary device members in at least two independent DOFs.

Moreover, the multi-functional limb movement auxiliary device comprises a bio-signal sensing unit that is configured to acquire bio-signals indicative of motor activity from the portion or remaining portion of the limb. Then, the multi-functional limb movement auxiliary device is equipped with a control unit that includes at least one processor unit and at least one digital data memory unit to which the at least one processor unit has data access. The control unit is configured to receive and evaluate the acquired bio-signals, with regard to estimating an intended movement, by carrying out a method comprising at least steps of digitally converting the acquired bio-signals, applying a novelty detection method for comparing the digitally converted, acquired bio-signals with data that reside in the at least one digital data memory unit and that represent bio-signals in response to a set of movements, and, based on a result of the comparison, for assigning a similarity measure to the digitally converted, acquired bio-signals, applying at least one sequential estimator to the digitally converted bio-signals, if the assigned similarity measure is equal to or larger than a pre-determined threshold value, and applying at least one simultaneous estimator to the digitally converted bio-signals, if the assigned similarity measure is smaller than the pre-determined threshold value.

The control unit is further configured to activate actuators out of the plurality of actuators, based on a result of applying the at least one sequential estimator or the at least one simultaneous estimator to the digitally converted bio-signals.

The phrase "limb movement auxiliary device", as used in this application, shall particularly encompass prostheses, movement-assisting orthoses, also known as "active" orthoses, exoskeletal devices and neurorehabilitation robotic devices, both for upper-extremities ("upper limb") and lower-extremities ("lower limb").

Simultaneous estimators are well known in the art and are described, by way of example, in J. M. Hahne et al., "Linear and nonlinear regression techniques for simultaneous and proportional myoelectric control", IEEE Trans. Neural Syst. Rehabil. Eng., vol. 22, no. 2, pp. 269-79, March 2014.

Sequential estimators are for instance described in K. Fukunaga: Introduction to Statistical Pattern Recognition, Second Edition, San Diego, Calif., USA: Academic Press, 1990.

Novelty detection methods are, for instance, known from M. Markou and S. Singh, "Novelty detection: a review-part 1: statistical approaches," Signal Processing, vol. 83, no. 12, pp. 2481-2497, December 2003.

The phrase "articulation", as used in this application, shall particularly encompass but not be limited to hinged joints, saddle joints and radial joints.

The movements in the at least two independent degrees of freedom shall encompass but not be limited to supination, pronation, flexion, extension, open hand, close hand, opposition grip and lateral grip.

The bio-signal sensing unit may be configured to sense bio-signals in an invasive or a non-invasive manner, and may be selected from a group encompassing, but not being limited to, a surface electromyogram device, a mechanomyogram device, a device comprising a mechanical sensor and/or a force/pressure sensor for sensing muscle bulging, a bio-impedance device, an electro-neurological device, a device acquiring signals directly from a muscle or a nerve in an invasive manner, an ultrasound device, an infrared device and a combination of any of these devices.

In this application, the phrase "bio-signal" shall be understood as a bio-signal that is indicative of a motor activity, if not explicitly expressed otherwise. The phrase "motor activity" shall in particular encompass muscular activity as well as neural activity.

The advantage of the disclosure is that it enables the user to elicit desired simultaneous movements in at least two independent DOFs for accomplishing a natural appearance of a prosthetic movement, as well as precise motions in a single DOF, if so intended by the user.

The disclosure is based on the insight that a combination of two state-of-the-art control methods can result in a limb movement auxiliary device capable of controlling at least movements in two DOFs simultaneously plus at least four additional movements in a sequential manner. This allows for very naturally-appearing movements, which are highly appreciated and demanded by users, while not having to limit the user to a control of two DOFs only, as would usually be the case with simultaneous estimator control only, plus allowing a more precise control in single DOF movements than a simultaneous estimator alone could provide. The control of the limb movement auxiliary device remains intuitive and direct, as would not be possible by multi-articulated limb movement auxiliary devices of the prior art.

In one embodiment, the data that reside in the at least one digital data memory unit and that represent bio-signals in response to a set of movements are computer-generated data.

In one embodiment, the socket member is an integral part of the base member.

In a preferred embodiment of the multi-functional limb movement auxiliary device, the novelty detection method is selected out of a group comprising, but not being limited to, One Class Support Vector Machine (OCSVM), Kernel Null Foley-Sammon Transform (KNFST), Mahalanobis distance (MD) approach and methods derived therefrom, such as MD-IND and MD-LDA, kNN-based approach and Common Spatial Patterns Proportional Estimator Likelihood (CSP-PELL).

One class support vector machine (OCSVM) was proposed by B. Scholkopf et al., "Support Vector Method for Novelty Detection," NIPS, vol. 12, pp. 582-588 (1999), and uses the kernel trick to map training data to a high-dimensional space such that they are compact and well separated from the origin in that space. That is, the smallest hypersphere in that space, which encloses all training data, is identified. For a newly applied sample it is evaluated whether it is inside or outside that hypersphere. This method is referred to as the gold standard solution in novelty detection.

The Kernel Null Foley-Sammon Transform (KNFST) was proposed by P. Bodesheim et al., "Kernel Null Space Methods for Novelty Detection", 2013 IEEE Conference on Computer Vision and Pattern Recognition, pp. 3374-3381, June 2013. It computes the Fisher linear discriminant analysis (LDA) transformation, while maximizing the between-class distance in the null space of the within-class scatter matrix i.e. the data are projected to a single point. This is only achievable in a high-dimensional space, such as obtained by applying a kernel transformation. In essence, the novel feature vector is mapped to the high-dimensional space and the minimum Euclidean distance of the transformed point to any of the trained class points is taken as the measure for novelty. An empirically determined threshold to that distance gives the decision for novelty or not. KNFST describes each trained base class individually and does not assume that all training data stem from the same class. In the present problem, multiple heterogeneous classes (training data per movement class) formed one super class of single-DOF movements.

The Mahalanobis distance (MD) approach is a relatively simple technique to calculate the minimum distance of a given feature vector to any of the training classes similarly to KNFST, but directly in the input space and without the Fisher transformation. As distance measure the Mahalanobis distance ($D_{Mahal}$) is suitable, assuming Gaussian distribution of each class. The $D_{Mahal}$ of a feature vector x to class i with the class mean vector pi and covariance matrix $\Sigma_i$ is calculated as:

$$D_{Mahal} = (x-\mu_i)^T \Sigma_i^{-1} (x-\mu_i)$$

In contrast to the kernel-based methods described before, this approach is computationally inexpensive and does not require hyperparameter optimization. However, a threshold for $D_{Mahal}$, above which a feature vector is classified as novel, has to be determined.

MD-IND is a variation that is mostly identical to the MD approach described above, with the difference that a novelty threshold for each movement class was determined individually.

MD-LDA is another variation of the MD approach and uses LDA transformation of the feature data before calculating $D_{Mahal}$ in the transformed space.

Rather than assuming an underlying Gaussian distribution of the class data and fitting the corresponding parameters as is carried out in the MD-based approaches, the nonparametric kNN approach was proposed for novelty detection by M. Markou and S. Singh in "Novelty detection: a review-part 1: statistical approaches," Signal Processing, vol. 83, no. 12, pp. 2481-2497, December 2003.

The approach is almost identical to MD, but rather than evaluating the minimal Mahalanobis distance of the feature vector to all classes, the minimal Euclidean distance to any set of k neighbors is considered.

In the CSP-PELL method, a further measure for recognition of known data can be extracted from the common spatial patterns proportional estimator (CSP-PE), introduced in S. Amsuess et al., "A Novel Multi-Class Proportional Myocontrol Algorithm for Upper Limb Prosthesis Control: Validation in Real-Life Scenarios on Amputees", submitted to and accepted as Early Access Paper by IEEE Transactions on Neural Systems and Rehabilitation Engineering (2014), pp. 1-10. As a part of the computation, the likelihood (CSP-PELL) of each estimation is obtained that can directly be used as an estimate for novelty. Again, a simple threshold value between 0 and 1 has to be selected.

In experimental studies, these novelty detection methods were found to be appropriate and beneficial for the intended purpose of comparing acquired bio-signals indicative of motor activity with data residing in the at least one digital data memory unit that represent motor activity data in response to movements in a single degree of freedom. Preferred methods are the kNN approach and the MD-IND and MD-LDA methods. The mostly preferred method is the Mahalanobis distance (MD) approach. In general, an employment of other novelty detection methods is also contemplated.

In another preferred embodiment of the limb movement auxiliary device, the data that reside in the at least one digital data memory unit represent bio-signals of a user of the limb movement auxiliary device. In this way, the bio-signals acquired from the portion or remaining portion of the limb can be dealt with on a user-individual basis, which can provide higher robustness for assigning the similarity measure to the acquired bio-signals.

In one embodiment, the data that reside in the at least one digital data memory unit represent at least one out of bio-signals in response to movements in a single degree of freedom, for all of the at least two independent degrees of freedom, or bio-signals in response to movements combining at least two degrees of freedom.

In one embodiment, the similarity measure can be obtained by comparing the digitally converted, acquired bio-signals to a set of stored training data.

In yet another preferred embodiment of the limb movement auxiliary device, the control unit is configured to periodically receive and evaluate bio-signals acquired in a time interval of specified duration, wherein the specified duration of the time interval is longer than the period time. In this way, a set of acquired bio-signals to be evaluated is partially updated by bio-signals acquired within the period time. By that, an especially smooth and naturally appearing prosthetic movement can be accomplished due to an averaging effect.

In one embodiment, the limb movement auxiliary device is designed as a human hand prosthesis and the socket member is configured to partially receive the remaining portion of a human forearm. In this way, an improved prosthesis can be provided for hand-amputees.

Preferably, the multi-functional limb movement auxiliary device further comprises at least one wireless data link between the bio-signal sensing unit and the control unit for wirelessly transferring the digitally converted, acquired bio-signals. In this way, a transfer of the acquired bio-signals can be accomplished without disturbing leads or cables, which provides higher comfort of use for the user.

In another aspect of the disclosure, a method of operating a multi-functional limb movement auxiliary device is provided. The multi-functional limb movement auxiliary device includes a base member, a socket member that is configured to at least partially receive a portion or remaining portion of a limb, and a plurality of limb movement auxiliary device members. Each limb movement auxiliary device member is connected in an articulated way to at least one out of the base member or a different limb movement auxiliary device member.

The multi-functional limb movement auxiliary device further comprises a plurality of actuators that are connectable to an electric power source. Each actuator is configured to move, upon activation, at least one limb movement auxiliary device member out of the plurality of limb movement auxiliary device members in an articulated way. The plurality of actuators is configured to enable articulated movements of limb movement auxiliary device members in at least two independent degrees of freedom.

Furthermore, the multi-functional limb movement auxiliary device includes an bio-signal sensing unit that is configured to acquire bio-signals indicative of motor activity from the portion or remaining portion of the limb: The multi-functional limb movement auxiliary device is equipped with a control unit that includes at least one processor unit and at least one digital data memory unit to which the at least one processor unit has data access. The control unit is configured to carry out the method, which comprises steps of acquiring bio-signals from the user of the limb movement auxiliary device, digitally converting the acquired bio-signals, applying a novelty detection method for comparing the acquired, digitally converted bio-signals with calibration bio-signals that reside in the at least one digital data memory unit, based on a result of the comparison, assigning a similarity measure to the acquired, digitally converted bio-signals, applying at least one sequential estimator to the acquired, digitally converted bio-signals, if the assigned similarity measure is equal to or larger than a pre-determined threshold value, applying at least one simultaneous estimator to the acquired, digitally converted bio-signals, if the assigned similarity measure is smaller than the pre-determined threshold value, and activating actuators out of the plurality of actuators, based on a result of the step of applying the at least one sequential estimator or the at least one simultaneous estimator to the acquired, digitally converted bio-signals.

By employing the method, the benefits described for the embodiments of the multi-functional limb movement auxiliary device can be accomplished.

In another embodiment, the method further comprises steps of acquiring bio-signals indicative of motor activity from a user of the limb movement auxiliary device while the user is executing a set of movements, and the set of movements includes at least one out of movements in a single degree of freedom, for all of the at least two independent degrees of freedom, or movements combining at least two degrees of freedom, digitally converting the acquired bio-signals, and storing the acquired, digitally converted bio-signals in the at least one digital data memory unit.

These steps of the method represent a calibration procedure. Further improvement of robustness for the step of comparing acquired bio-signals with the digitally converted calibration bio-signals can readily be accomplished by extending or updating the acquired, digitally converted calibration bio-signals.

In yet another aspect of the present disclosure, a software module is provided for carrying out steps of an embodiment of the disclosed method of operating a multi-functional limb movement auxiliary device. The method steps to be conducted are converted into a program code of the software module, wherein the program code is implementable in a digital data memory unit of the multi-functional limb movement auxiliary device and is executable by a processor unit of the multi-functional limb movement auxiliary device.

The software module can enable a robust and reliable execution of the method and can allow for a rapid modification of method steps.

These and other aspects of the disclosure will be apparent from and elucidated with reference to the embodiments described hereinafter. Such embodiment does not necessarily represent the full scope of the disclosure, however, and reference is made therefore to the claims and herein for interpreting the scope of the disclosure.

THE DRAWINGS

The drawings described herein are for illustrative purposes only of selected embodiments and not all possible implementations, and are not intended to limit the scope of the present disclosure.

Figure 2:
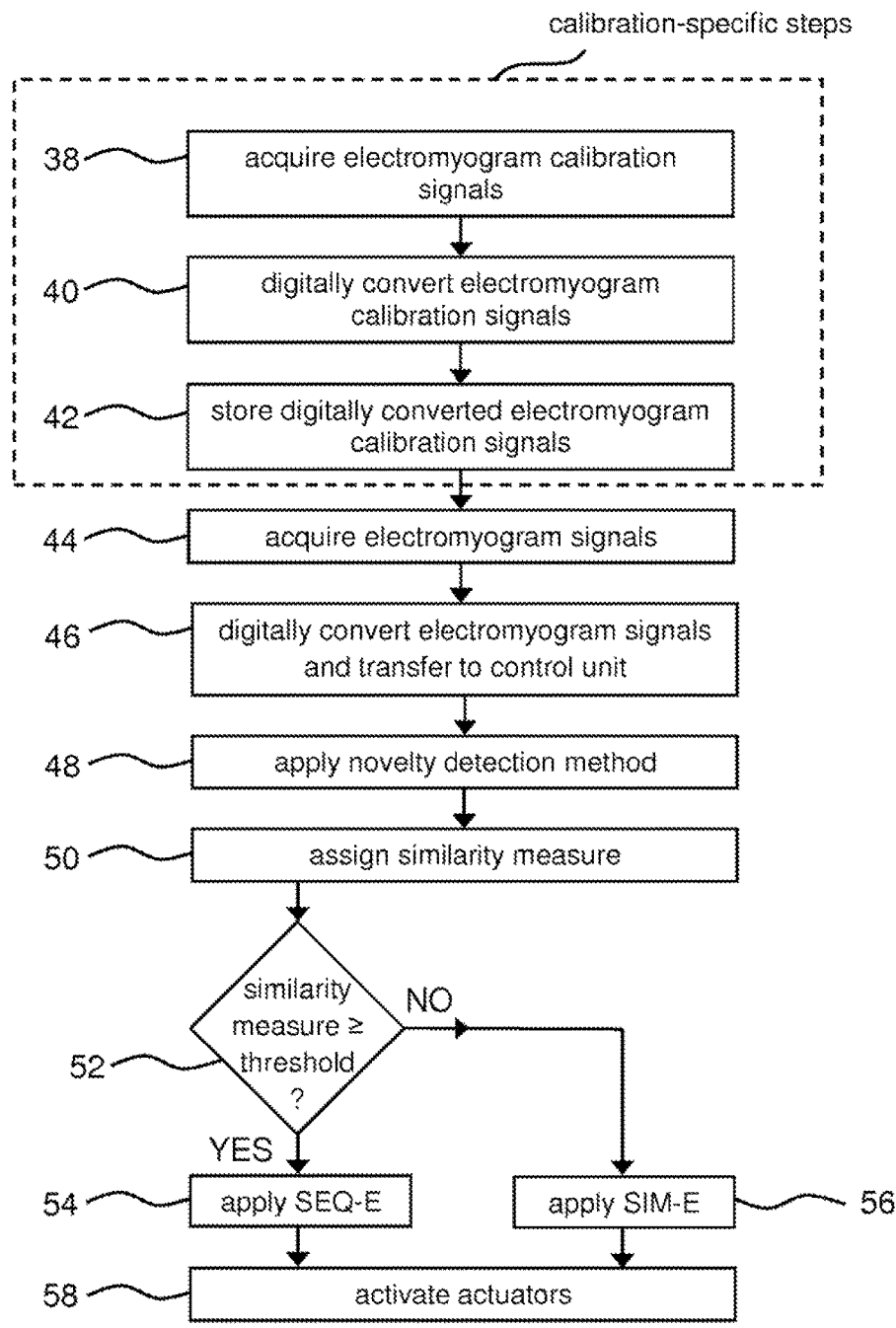
Figure 3:
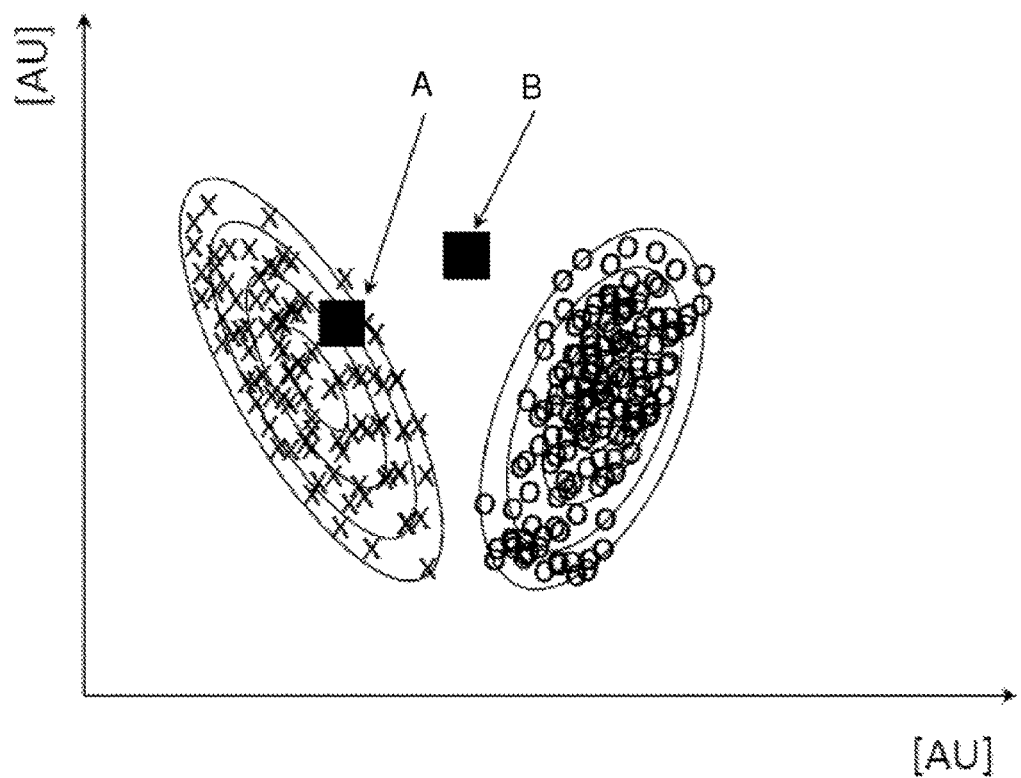
Figure 4:
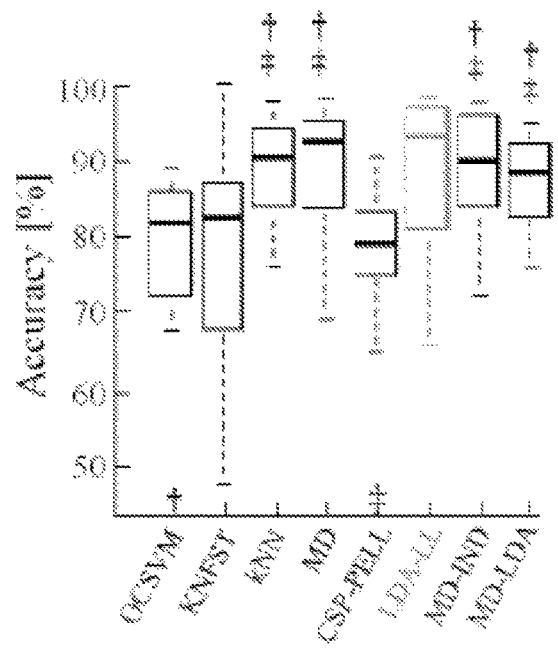

In the drawings:

FIG. 1 schematically shows a multi-functional limb movement auxiliary device in accordance with the disclosure, FIG. 2 is a flowchart of an embodiment of the method of operating the multi-functional limb movement auxiliary device pursuant to FIG. 1 in accordance with the disclosure, FIG. 3 exemplarily illustrates results of applying a novelty detection method for comparing acquired bio-signals indicative of motor activity with data that reside in a digital data memory unit, and FIG. 4 depicts experimental results regarding accuracy of recognition for various novelty detection methods employed in the method pursuant to FIG. 2.

Corresponding reference numerals indicate corresponding parts throughout the several views of the drawings.

DETAILED DESCRIPTION

Example embodiments will now be described more fully with reference to the accompanying drawings.

FIG. 1 shows a multi-functional limb movement auxiliary device in accordance with the disclosure, without loss of generality being designed as a transradial hand prosthesis. The transradial hand prosthesis comprises a base member 10 and a socket member 12 that is configured to partially receive a remaining portion of a forearm 14 of a user of the prosthesis. The base member 10 and the socket member 12 are integrally formed. The transradial hand prosthesis includes a plurality of limb movement auxiliary device members formed as a thumb, fingers, palm and wrist. Thumb and fingers are connected in an articulated way by a saddle joint and hinge joints, respectively, to the palm. The wrist is connected to the base member 10 in an articulated way by a radial joint.

The transradial hand head prosthesis further comprises a plurality of actuators (not shown) connected to the electric power source formed by a battery pack 22 that is received in a recess of the base member 10. Each actuator of the plurality of actuators is configured to move, upon activation, at least one of the limb movement auxiliary device members in an articulated way according to the type of articulation.

The plurality of actuators enables seven articulated single-degree of freedom (DOF) movements: wrist supination, wrist pronation, wrist flexion, wrist extension, hand open, opposition grip and lateral grip, so that the transradial hand prosthesis provides 3.5 DOFs that are controllable by the user.

Moreover, the transradial hand prosthesis includes a biosignal sensing unit 16 that is designed, without limitation, as an electromyogram sensing unit that is configured to acquire motor activity signals formed by electromyogram signals from a surface of the remaining portion of the forearm 14. The electromyogram sensing unit comprises an elastic carrier member 18 made from a plastic material and having a curved shape to match a curvature of the forearm 14. In this way, the elastic carrier member 18 can readily be attached to and detached from the forearm 14. The electromyogram sensing unit comprises a plurality of metal electrodes 20 securely held in openings of the elastic carrier member 18 and being in contact with the surface of the forearm 14 when the elastic carrier member 18 is attached to the forearm 14 for acquiring electromyogram signals.

Furthermore, the transradial hand prosthesis comprises a control unit 24 that includes a processor unit 26, a RAM-type digital data memory unit 28 and a ROM-type digital data memory unit 30. The processing unit 26 has data access to both the RAM-type digital data memory unit 28 and the ROM-type digital data memory unit 30.

The control unit 24 includes an analog-to-digital converter 34 (ADC) that is attached to the elastic carrier member 18 of the electromyogram sensing unit. Each metal electrode 20 of the plurality of metal electrodes 20 is connected to an input port of the ADC 34 via a multiplexer and an anti-analyzing filter (not shown). The ADC 34 is configured to digitize acquired electromyogram signals at a sample rate of 1 kHz and with 10 bit depth.

Then, the transradial hand prosthesis comprises a wireless data link 36 between the electromyogram sensing unit and the control unit 24 for wirelessly transferring the acquired electromyogram signals. An output port of the ADC 34 is connected to the wireless data link 36. In this specific embodiment, the wireless data link 36 is designed as a Bluetooth® data link, but any other wireless data link that appears suitable to those skilled in the art may be employed. Both the wireless data link 36 and the ADC 34 are powered by a battery that is installed in a recess of the elastic carrier member 18 (not shown).

In the following, an embodiment of a method in accordance with the disclosure of operating the multi-functional limb movement auxiliary device designed as a transradial hand prosthesis is described. A flowchart of the method is given in FIG. 2. It shall be understood that all involved units and devices are in an operational state and configured as illustrated in FIG. 1.

In order to be able to carry out the method, the control unit 24 comprises a software module 32 (FIG. 1). The method steps to be conducted are converted into a program code of the software module 32, wherein the program code is implemented in the RAM-type digital memory unit 28 of the control unit 24 and is executable by the processor unit 26 of the control unit 24.

In a first step 38 of a calibration-specific portion of the method, electromyogram calibration signals are acquired from the user of the transradial hand prosthesis while the user is executing a set of movements. Each movement of the set of movements has a single degree of freedom, and the set of movements includes movements for all of the 3.5 independent DOFs. The control unit 24 is configured to periodically receive and evaluate electromyogram signals acquired in a time interval with a duration of 150 ms, with a period time of 30 ms.

In the next step 40 of the calibration, the acquired electromyogram calibration signals are digitally converted. In a following step 42, the digitally converted electromyogram calibration signals are stored in the ROM-type digital data memory unit 30. A 2D-representation of an example of digitally converted electromyogram calibration signals is shown in FIG. 3. The cross symbols represent electromyogram calibration signals in response to one of the single-DOF movements. The open circle symbols represent electromyogram calibration signals in response to a different one of the single-DOF movements. The 2D-representation has been obtained by principal component analysis. Mahalanobis equidistance contours are added for assessment purposes.

In principle, the steps 38-42 of the calibration-specific portion of the method have to be carried out only once, except for a desired or required extending or updating of the digitally converted, stored electromyogram calibration signals.

Then, in a step 44 of the method, electromyogram signals are acquired from the user of the transradial hand prosthesis. The acquired electromyogram signals are digitally converted and transferred from the electromyogram sensing unit to the control unit 24 via the wireless data link 36 in a next step 46.

In a next step 48 of the method, a novelty detection method ND formed by the Mahalanobis distance (MD) approach is applied to the acquired electromyogram signals for comparing the acquired electromyogram signals with the digitally converted electromyogram calibration signals that reside in the ROM-type digital data memory unit 30.

In another step 50, based on the results of the step 52 of comparison, a similarity measure is assigned to the acquired electromyogram signal. In the example shown in FIG. 3, a similarity measure larger than a pre-determined threshold value is assigned to the acquired electromyogram signal labeled "A", and the corresponding movement is assessed to be similar to a single-DOF movement in step 52. In a next step 54, a sequential estimator SEQ-E is applied to the digitally converted electromyogram signals.

Referring again to FIG. 3, a similarity measure that is smaller than the pre-determined threshold value is assigned to the acquired electromyogram signal labeled "B", and the corresponding movement is assessed to be dissimilar to a single-DOF movement in step 52. In a next step 56, a simultaneous estimator SIM-E is applied to the digitally converted electromyogram signals.

As the result of applying the novelty detection method ND is that the acquired electromyogram signal labeled "B" is dissimilar to any of the digitally converted electromyogram calibration signals obtained in the course of calibration, it is considered novel, consequently has to be of different origin than the single-DOF movement that generated the digitally converted electromyogram calibration signals, and therefore has to have been generated by a combined motion. In this case, the simultaneous estimator SIM-E is used for controlling the transradial hand prosthesis.

In a final step 58 then, actuators out of the plurality of actuators are activated, based on a result of the step 54 of applying the sequential estimator SEQ-E or the step 56 of applying the simultaneous estimator SIM-E to the digitally converted electromyogram signals.

FIG. 4 depicts experimental results regarding accuracy of recognition of single-DOF movements for other novelty detection methods ND that are also employable in the method pursuant to FIG. 2. Due to the highest level of accuracy, the Mahalanobis distance (MD) approach is the most preferred novelty detection method.

While the disclosure has been illustrated and described in detail in the drawings and foregoing description, such illustration and description are to be considered illustrative or exemplary and not restrictive; the disclosure is not limited to the disclosed embodiments. Other variations to the disclosed embodiments can be understood and effected by those skilled in the art in practicing the claimed disclosure, from a study of the drawings, the disclosure, and the appended claims. In the claims, the word "comprising" does not exclude other elements or steps, and the indefinite article "a" or "an" does not exclude a plurality. Plurality is to be understood as at least two or more, unless specified otherwise. The mere fact that certain measures are recited in mutually different dependent claims does not indicate that a combination of these measures cannot be used to advantage. Any reference signs in the claims should not be construed as limiting the scope.

The invention claimed is:

1. A multi-functional limb movement auxiliary device, comprising
    a base member,
    a socket member that is configured to at least partially receive a portion or remaining portion of a limb,
    a plurality of limb movement auxiliary device members, each limb movement auxiliary device member being connected in an articulated way to at least one of the base member or a different limb movement auxiliary device member,
    a plurality of actuators that are connectable to an electric power source, wherein each actuator is configured to move, upon activation, at least one limb movement auxiliary device member out of the plurality of limb movement auxiliary device members in an articulated way, and wherein the plurality of actuators is configured to enable articulated movements of limb movement auxiliary device members in at least two independent degrees of freedom,
    a bio-signal sensing unit that is configured to acquire bio-signals indicative of motor activity from the portion or remaining portion of the limb,
    a control unit, including at least one processor unit and at least one digital data memory unit to which the at least one processor unit has data access, the control unit being configured to
    receive and evaluate the acquired bio-signals to estimate an intended movement, by carrying out steps comprising
        digitally converting the acquired bio-signals,
        applying a novelty detection method for comparing the digitally converted, acquired bio-signals with data that reside in the at least one digital
        data memory unit and that represent bio-signals in response to a set of movements, and, based on a result of the comparison,
        assigning a similarity measure to the digitally converted, acquired bio-signals,
        applying at least one sequential estimator (SEQ-E) to the digitally converted bio-signals, if the assigned similarity measure is equal to or larger than a pre-determined threshold value,
        applying at least one simultaneous estimator (SIM-E) to the digitally converted bio-signals, if the assigned similarity measure is less than the pre-determined threshold value,
    and the control unit is further configured to activate at least one actuator out of the plurality of actuators, based on a result of applying the at least one sequential estimator (SEQ-E) or the at least one simultaneous estimator (SIM-E) to the digitally converted bio-signals.

2. The multi-functional limb movement auxiliary device as claimed in claim 1, wherein the novelty detection method (ND) is selected out of a group comprising One Class Support Vector Machine (OCSVM), Kernel Null Foley-Sammon Transform (KNFST), Mahalanobis distance (MD) approach, Mahalanobis distance-Individual (MD-IND), Mahalanobis distance lineal discriminant analysis (MD-LDA), k-nearest neighbors (kNN)-based approach, or Common Spatial Patterns Proportional Estimator Likelihood (CSP-PELL).

3. The multi-functional limb movement auxiliary device as claimed in claim 1, wherein the data stored in the at least one digital data memory unit represent bio-signals of a user of the limb movement auxiliary device.

4. The multi-functional limb movement auxiliary device as claimed in claim 1, wherein the data stored in the at least one digital data memory unit represent at least one out of
- bio-signals in response to movements in a single degree of freedom, for all of the at least two independent degrees of freedom, or
- bio-signals in response to movements combining at least two degrees of freedom.

5. The multi-functional limb movement auxiliary device as claimed in claim 1, wherein the control unit is configured to set a period time to periodically receive and evaluate bio-signals acquired in a time interval of specified duration, wherein the specified duration of the time interval is longer than the period time.

6. The multi-functional limb movement auxiliary device as claimed in claim 1, wherein the limb movement auxiliary device is designed as a human hand prosthesis, and wherein the socket member is configured to partially receive the remaining portion of a human forearm.

7. The multi-functional limb movement auxiliary device as claimed in claim 1, further comprising at least one wireless data link between the bio-signal sensing unit and the control unit for wirelessly transferring the digitally converted, acquired bio-signals.

8. A method of operating a multi-functional limb movement auxiliary device, the limb movement auxiliary device comprising
- a base member,
- a socket member that is configured to at least partially receive a portion or remaining portion of a limb,
- a plurality of limb movement auxiliary device members, each limb movement auxiliary device member being connected in an articulated way to at least one of the base member or a different limb movement auxiliary device member,
- a plurality of actuators that are connectable to an electric power source, wherein each actuator is configured to move, upon activation, at least one limb movement auxiliary device member out of the plurality of limb movement auxiliary device members in an articulated way, and wherein the plurality of actuators is configured to enable articulated movements of limb movement auxiliary device members in at least two independent degrees of freedom,
- a bio-signal sensing unit that is configured to acquire bio-signals indicative of motor activity from the portion or remaining portion of the limb, and
- a control unit, including at least one processor unit and at least one digital data memory unit to which the at least one processor unit has data access, the method comprising steps of
- acquiring bio-signals from the user of the limb movement auxiliary device,
- digitally converting the acquired bio-signals,
- applying a novelty detection method (ND) for comparing the acquired, digitally converted bio-signals with calibration bio-signals that reside in the at least one digital data memory unit,
- based on a result of the comparison, assigning a similarity measure to the acquired, digitally converted bio-signals,
- applying at least one sequential estimator (SEQ-E) to the acquired, digitally converted bio-signals, if the assigned similarity measure is equal to or larger than a pre-determined threshold value,
- applying at least one simultaneous estimator (SIM-E) to the acquired, digitally converted bio-signals, if the assigned similarity measure is smaller than the pre-determined threshold value, and
- activating at least one actuator out of the plurality of actuators, based on a result of the step of applying the at least one sequential estimator (SEQ-E) or of applying the at least one simultaneous estimator (SIM-E) to the acquired, digitally converted bio-signals.

9. The method as claimed in claim 8, further comprising steps of
- acquiring bio-signals indicative of motor activity from a user of the limb movement auxiliary device while the user is executing a set of movements, and the set of movements includes at least one movement in a single degree of freedom or movements combining at least two degrees of freedom,
- digitally converting the acquired bio-signals, and
- storing the acquired, digitally converted bio-signals in the at least one digital data memory unit.

10. The method as claimed in claim 8, wherein the novelty detection method (ND) is selected out of a group comprising One Class Support Vector Machine (OCSVM), Kernel Null Foley-Sammon Transform (KNFST), Mahalanobis distance (MD), Mahalanobis distance-Individual (MD-IND), Mahalanobis distance lineal discriminant analysis (MD-LDA), k-nearest neighbors (kNN)-based approach, or Common Spatial Patterns Proportional Estimator Likelihood (CSP-PELL).

11. The method as claimed in claim 8, further comprising a software module for carrying out the method steps, wherein the method steps to be conducted are converted into a program code of the software module, wherein the program code is implementable in a digital data memory unit of the multi-functional limb movement auxiliary device and is executable by a processor unit of the multi-functional limb movement auxiliary device.

* * * * *